United States Patent [19]

Maganias

[11] Patent Number: 4,966,159
[45] Date of Patent: Oct. 30, 1990

[54] ALLERGY TEST STRIP

[76] Inventor: Nicholas H. Maganias, Reston Medical Bldg., 1712 Club House Rd., Reston, Va. 22090

[21] Appl. No.: 644,941

[22] Filed: Aug. 27, 1984

Related U.S. Application Data

[63] Continuation-in-part of Ser. No. 445,746, Nov. 30, 1982, abandoned, which is a continuation-in-part of Ser. No. 330,587, Dec. 14, 1981, Pat. No. 4,473,083.

[51] Int. Cl.⁵ .............................................. A61B 5/00
[52] U.S. Cl. ...................................... 128/743; 604/46
[58] Field of Search ..................... 128/743; 604/46, 47

[56] References Cited

U.S. PATENT DOCUMENTS

| | | | |
|---|---|---|---|
| 3,289,670 | 12/1966 | Krug et al. ........................... | 128/743 |
| 3,977,392 | 8/1976 | Manley ................................. | 128/641 |
| 4,177,817 | 12/1979 | Bevilacqua ........................... | 128/803 |

Primary Examiner—Max Hindenburg
Assistant Examiner—John P. Lacyk
Attorney, Agent, or Firm—Cushman, Darby and Cushman

[57] ABSTRACT

A test strip for allergy testing the skin includes a support lamina having at least one aperture extending therethrough and a lance device positioned on one surface of the support lamina so that the sharp lance of the device extends into the aperture. A removable strip is releasably sealed to the opposite surface of the support lamina and overlies the aperture to prevent entry of foreign material into the aperture. Upon removal of the strip an allergen can be applied through the aperture to the lance. A second strip overlies the lance device and is removably sealed to the support lamina. Upon removal of the second strip the lance device is also removed from the support lamina so that the second strip and the lance device can be applied to the skin.

14 Claims, 2 Drawing Sheets

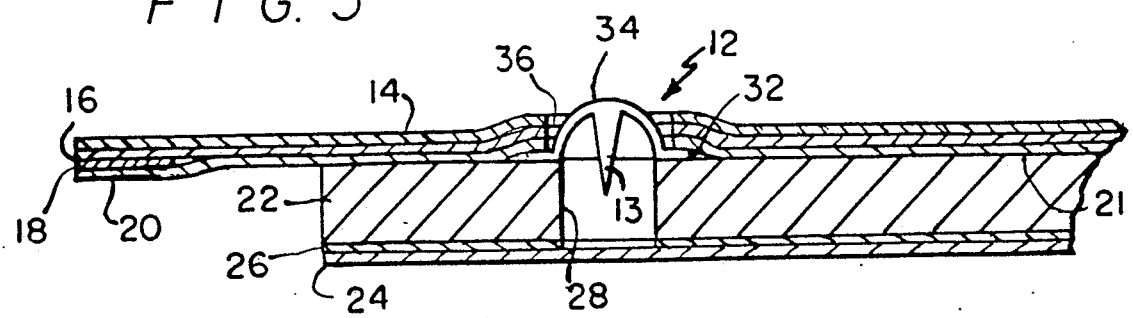
FIG. 5
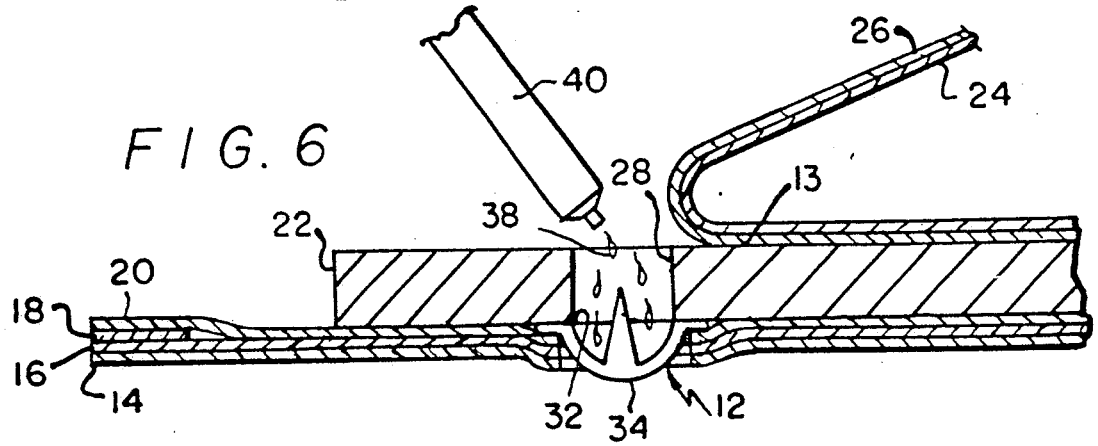
FIG. 6
FIG. 7
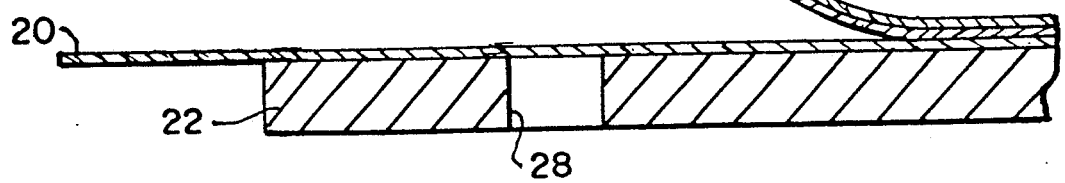
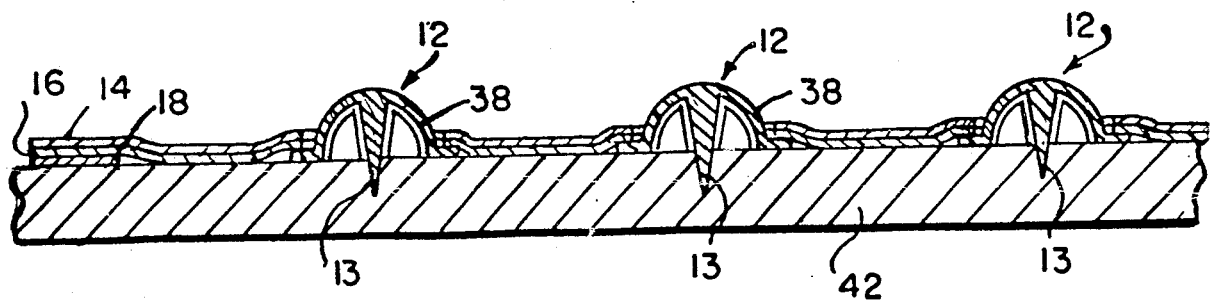
FIG. 8

ALLERGY TEST STRIP

This application is a continuation-in-part of application Ser. No. 445,746 filed Nov. 30, 1982 now abandoned which is a continuation-in-part of application Ser. No. 330,587, filed Dec. 14, 1981, now U.S. Pat. No. 4,473,083.

This invention relates to a test strip for allergy testing the skin of a patient.

BACKGROUND

Testing the skin of a patient for an allergic reaction to any of a variety of allergens is a known technique involving penetration of the allergen into a small area of the skin and subsequently visually observing the reaction, if any, of the skin to the allergen. Known procedures for applying the allergen include the scratch test, the prick test and the intradermal test. The scratch test is carried out by applying a few drops of the allergen to the skin and slightly abrading the skin by scratching at that location. The prick test is similar except that abrasion of the skin is effected by making a plurality of pricks with a sharp needle. The intradermal test is carried out by injecting the allergen into the skin.

U.S. patents relating to the introduction of biochemical substances into the skin include U.S. Pat. Nos. 2,304,817, to Grozin, 2,817,336, (and Re. 25,637), to Kravitz et al, 2,893,392, to Wagner et al, 3,062,212, to Kravitz et al, 3,072,122, to Rosenthal, 3,136,314, to Kravitz, 3,556,080, to Hein, 3,814,097, to Ganderton et al, 3,964,482 to Gerstel et al, and 4,304,241 to Brennan.

SUMMARY OF THE INVENTION

The present invention is based in part on the observation that each of the scratch test, the prick test and the intradermal test has one or more disadvantages. The scratch test may not produce enough scarification of the skin and thus lead to an inaccurate conclusion due to insufficient skin cell damage to permit adequate entry of and reaction with the allergen. The prick test may produce excessive trauma, for example, microbleeding, which can produce histamine release thereby confusing the results of the test. With the intradermal test it is frequently difficult to titrate the degree of skin reaction and large and often false positive reactions develop. Each procedure has its own advantages, however. The medical practitioner will generally decide on which procedure to use taking into consideration the time required for the test, pain inflicted on the patient, trauma to the skin, weak reactions, expense and other features.

The present invention provides an allergy test strip which combines a number of the advantages of the usual procedures while avoiding or reducing the disadvantages referred to above.

The test strip is a laminate which includes three primary layers in addition to at least one lance device. Normally the test strip is an elongated strip carrying a plurality of longitudinally spaced-apart lance devices, but the principles of the invention apply equally well to a single lance device. The first or intermediate layer is a relatively thick protective layer which surrounds at least the lance portion of the lance device so as to provide protection against damage. While the lance device or at least the lance portion of the device may be merely embedded in the intermediate layer, it is preferred that the lance portion fit into a hole in the intermediate layer such that the lance portion is accessible through one end of the hole. In conjunction with the other two layers the intermediate layer also serves to support the lance device and to provide a sealed package for the lance device to maintain the latter in a sterile condition. The material of construction of the intermediate layer may be flexible plastic foam.

The second layer is a lance-carrying layer releasably attached to the intermediate layer. The lance device is attached sufficiently firmly to this second layer that when the latter is removed or detached from the intermediate layer, the lance device remains with the second layer. The second layer is preferably a flexible strip of adhesive tape which releasably adheres to one surface of the intermediate layer. The lance device is also adhered to the adhesive surface of the tape or is otherwise attached to the latter. When the tape is thus attached to the intermediate layer, the lance portion of the lance device projects into the hole in the intermediate layer, and the seal between the tape and the intermediate layer prevents contact of foreign matter with the lance device. In the embodiment described hereinafter the lance device is a hollow, generally semispherical dome having an internal concave surface providing a cavity for allergen and a peripheral radially extending flange around the rim of the cavity. The lance projects from the concave surface to a location outside the cavity. The adhesive tape can overlie the convex surface of the dome and the adjacent surface of the flange, or the tape may have an aperture of a size large enough to permit the dome but not the flange to protrude therethrough. The precise structure and material of construction of the lance device is not critical to the three-layer laminated test strip of the present invention.

The third layer is a closure layer releasably attached to the opposite surface of the intermediate layer from the first or lance-carrying layer. This closure layer, which may be a flexible strip of adhesive tape, closes the hole in which the lance portion of the lance device resides and seals to the intermediate layer to prevent entry of foreign matter. The closure layer is, however, readily strippable from the intermediate layer to expose the lance.

In using the test strip the practitioner strips the closure layer from the intermediate layer and applies allergen to the lance. The lance-carrying layer, with the attached lance device, is then stripped from the intermediate layer and is pressed against the skin of a patient so that the layer releasably adheres to the skin. The lance device is then pressed with the fingers to cause the lance or lances to penetrate the skin to a depth less than the subcutaneous tissue thereby carrying some of the allergen into the skin and maintaining constant contact between the allergen and the traumatized skin cells. After a period of time appropriate for the skin to react with the allergen, for example 15 to 20 minutes, the lance-carrying layer including the lance or lances is removed from the skin and discarded. The degree of skin reaction, in terms of inflammation, swelling or the formation of protuberances, and hence the degree of allergy is then determined by the medical practitioner by visually observing the area of skin which was punctured by the lance or lances. Several such tapes, each carrying a different allergen, can be applied to the skin simultaneously or essentially simultaneously. Alternatively a single tape can carry a plurality of lances or groups of lances, each lance or group carrying a different allergen. The appearance of the skin area may be compared to one or more control skin areas which have been similarly punctured by similar test strips having a lance or lances free of allergen.

In this description, the term layer or lamina is not intended to be restricted to a single thickness of a given material. That is, a layer may itself include more than one stratum.

BRIEF DESCRIPTION OF THE DRAWINGS

FIG. 5 is a sectional view, on an enlarged scale, taken on the line 5—5 of FIG. 3;

FIG. 6 is a sectional view, on an enlarged scale, taken on the line 6—6 of FIG. 4, modified to illustrate the application of allergen to the lances of the test strip;

FIG. 7 is a sectional view similar to FIG. 5, modified to illustrate removal of the lances from the protective portion of the test strip; and FIG. 8 is a sectional view illustrating application of the lances to the skin of a patient.

In all of the views, the thickness of some of the layers, especially the layers of adhesive, has been exaggerated for clarity.

DETAILED DESCRIPTION

Figure 2:
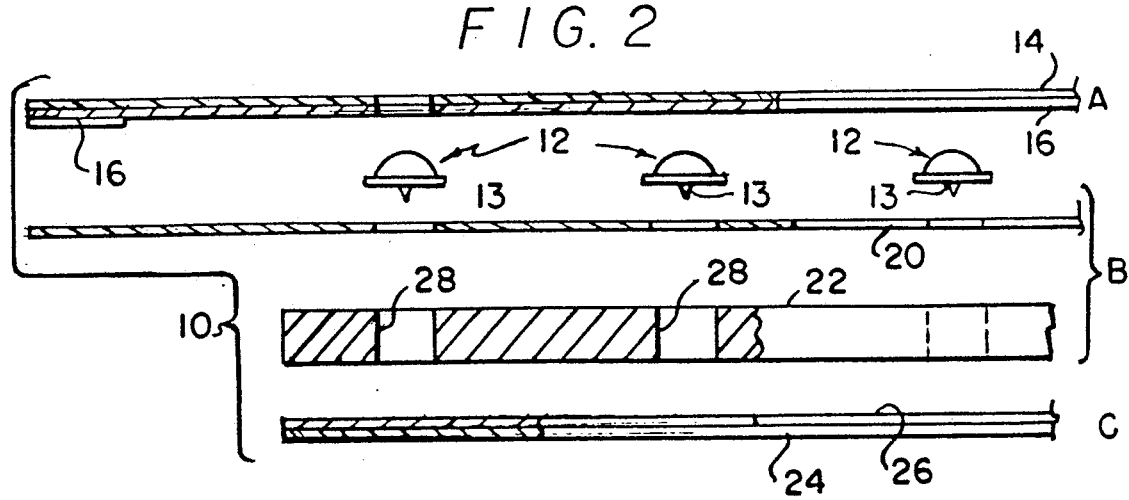
FIG. 2 is an exploded side elevational view of the test strip of FIG. 1.
Figure 3:
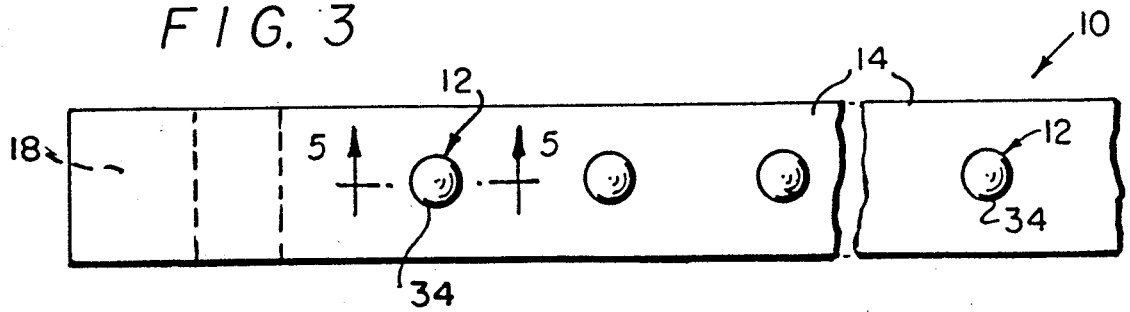
FIG. 3 is a plan view of the test strip of FIG. 1.

The drawings illustrate an allergy test strip 10 which embodies the principles of the present invention. The strip is elongate and carries a plurality of lance devices 12 which are spaced-apart along the length of the strip. Each lance device includes at least one lance 13 which in use of the test strip 10 will penetrate the skin of a patient. As shown in FIG. 2, the illustrated embodiment includes three primary layers or laminae A, B and C which in combination support the lance devices 12 in a special way.

Lamina A is a lance-carrying strip of adhesive tape in the form of a thin flexible plastic film 14 carrying on one of its surfaces a layer of pressure sensitive adhesive 16. As lamina A is to be stripped off with the fingers during use, it includes at either or both ends a short strip 18 or tab of non-adhesive tape or paper which covers the adhesive 16 so as to prevent the end of lamina A from adhering to lamina B. The adhesive 16 contacts and adheres to the lance devices 12 so that when lamina A is stripped from lamina B, the lance devices 12 remain attached to lamina A as described in detail below.

Figure 1:
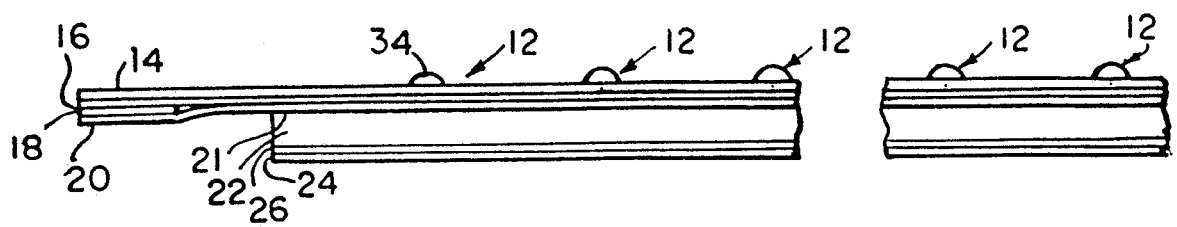
FIG. 1 is a side elevational view of a test strip embodying the principles of the present invention.

Intermediate lamina B is a protective and support lamina including a relatively thick stratum 22 of material which protects the lance devices 12 from damage during storage. In the illustrated embodiment the material is a plastic foam material bonded to the adjacent surface of a thin flexible strip 20 of material having a release surface facing the adhesive surface 16 of lamina A so that laminae A and B can be releasably sealed together. The strip 20 in the illustrated embodiment is paper having a thin coating of release material on the surface facing lamina A. The opposite surface of the strip 20 is attached to lamina B in a generally non-detachable manner as by being heat-bonded to lamina B at 21 (FIGS. 1 and 5) or by means of a non-releasable adhesive (not shown).

Lamina C is a closure layer in the form of a strip of adhesive tape which includes a thin plastic film 24 and a layer of pressure sensitive adhesive 26 on the side of the film 24 facing lamina B. As described more in detail below, lamina C, when stripped from lamina B, permits an allergen to be applied to the lance devices 12 (FIG. 6).

It will be seen that the ends of lamina A and the strip 20 project beyond the end of the layer 22. This is merely an aid in manipulating the test strip 10 during use as described below. In some cases, the layer 22 is not strictly necessary so long as lamina A together with the lance devices can be stripped from the layer 22.

Figure 4:
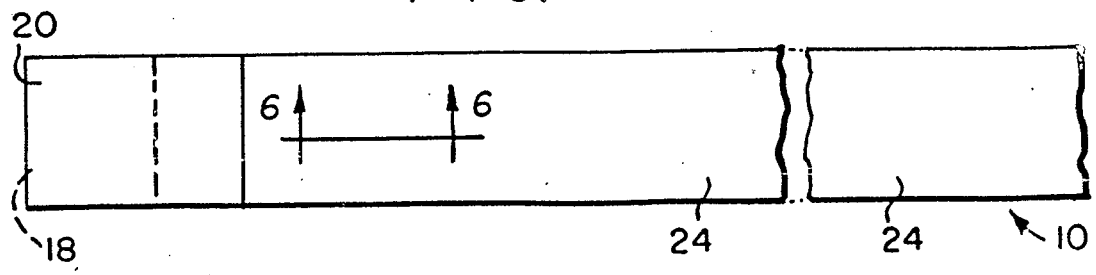
FIG. 4 is a bottom view of the test strip of FIG. 1.

The illustrated lance devices 12 are of the type illustrated in FIG. 4 of copending application Ser. No. 445,746 filed Nov. 30, 1982. While this form of lance device is preferred, the present invention is not limited thereto, as the essential features of the present invention are the lance-support layer, a strippable lance-carrying layer which can be stripped together with the lances from the support layer and a strippable closure layer which, when removed from the support layer, exposes the lances for application of allergen.

FIGS. 1, 3, 4 and 5 illustrate the test strip 10 before use and as stored by the physician. The lance devices 12 are maintained sterile by the sealing action between the vearious layers of the test strip 10. The adhesive tape 14,16 carries the lance devices 12 and is releasably attached to the release layer 20 which in turn is bonded to the support layer 22. The support layer 22 is provided with apertures 28 which receive and surround the projecting lances 13 of each lance device 12. The layer 20 has holes 30 of the same size as and coinciding with the holes 28. The peripheral flange 32 of each lance device rests on the rim of the respective hole 30 and is held in place by the adhesion of the adhesive tape 14,16 to the flanges 32 and to the paper layer 20. The dome-shaped portions 34 of the lance devices 12 project through holes 36 in the adhesive tape 14,16. Alternatively the adhesive tape 14,16 may be free of holes and thereby completely overlie the dome-shaped portions 34.

The closure 24,26 is releasably sealed to the surface of the support layer 22 opposite the lance devices 12. The tape 24,26 thereby closes the apertures 28 in the layer 22 to prevent entry of foreign matter but is strippable from the layer 22.

To carry out an allergy test the test strip 10 is first oriented with the closure tape 24,26 facing upwards, as shown in FIG. 6. The closure tape 24,26 is then manually stripped from the support layer 22 thereby uncovering the holes 28 and exposing the lances 13 of the lance devices, also as shown in FIG. 6. Liquid allergen 38 is then supplied from a pipette 40 or other applicator to the concave cavity of each lance device 12. Alternatively if the allergen is in dry form the practitioner will apply several drops of sterile water to the cavity to dissolve or disperse the dry allergen. In either case the liquid coats the surface of the cavity and the lance 13 and is held in place by surface tension forces. A further alternative is that the allergen can be supplied to the lance cavity prior to use of the test strip 10, in which case the allergen is already present in the test strip illustrated in FIG. 5. The allergen supplied to the lance devices 12 may be the same for all devices 12 or different for each device 12.

Next, the lance-carrying tape 14,16, together with the attached lance devices 12, is stripped from the layer 20,22. This step is illustrated in FIG. 7 and is shown being carried out with the test strip being oriented with the tape 14,16 facing upwardly. The stripping step can also be carried out with the tape 14,16 facing downwardly.

The adhesive side of the tape 14,16 and its attached lance devices 12 is then applied to the skin 42 to hold the lance devices 12 in place, as shown in FIG. 8. Simultaneously or subsequently the practitioner gently and firmly presses with his fingers each lance device 12 to cause the latter to penetrate the skin. The liquid allergen is thus carried partly into the skin and is maintained in constant contact with the thus traumatized skin cells until the tape and devices are removed. A contact time of 15–20 minutes is generally suitable and upon removal the practitioner observes the punctured skin areas to determine the extent of allergic reaction. The punctured skin areas can be compared to adjacent skin areas which have been punctured by allergen-free lances of a control test strip of the same or similar construction. The materials of the tape 14,16 may be essentially transparent and colorless in which case the skin reactions can be observed through the tape 14,16.

What is claimed is:

1. A laminated test strip for allergy testing by a technique involving penetration of an allergen into the skin comprising: at least one lance device having at least one lance projecting therefrom; a support lamina having opposite surfaces and an aperture extending through the lamina from one of said surfaces to the other, said lance device being positioned on one of said surfaces with said lance extending into said aperture in said support lamina; a first removable lamina releasably sealed to the surface of said support lamina opposite the surface on which said lance device is positioned and overlying said aperture to prevent entry of foreign material into said aperture but upon being removed from said opposite surface of said support lamina permitting an allergen to be applied to said lance; a second removable lamina releasably sealed to said one surface of said support lamina, said lance device being attached to said second removable lamina so that upon removal of said second removable lamina said lance device is also removed and can be applied to the skin.

2. A test strip as in claim 1 wherein said lance device has a recessed surface forming a cavity, said at least one lance projecting from said recessed surface to a point outside said cavity.

3. A test strip as in claim 1 wherein said lance device is a generally semi-spherical structure having an imperforate dome-shaped body forming a concave cavity from which said at least one lance projects, said structure further having a peripheral flange around the cavity.

4. A test strip as in claim 1 including a plurality of spaced-apart lance devices, said support lamina and said first and second removable laminae being common to all said plurality of lance devices.

5. A laminated test strip for allergy testing by a technique involving penetration of an allergen into the skin comprising: at least one lance device having at least one lance projecting therefrom, said lance device being attached to one surface of a flexible film with said lance projecting away from said surface; a support laminae having opposite surfaces and an aperture extending through the lamina from one of said surfaces to the other, said film being detachably sealed to one surface of said support lamina such that said lance projects into said aperture in said support lamina; and a closure lamina detachably sealed to the opposite surface of said support lamina so as to overlie said aperture in said support lamina to prevent entry of foreign material into said aperture whereby upon removal of said closure lamina, from said support lamina, allergen can be applied to said lance, and whereby removal of said film and its attached lance device from said support lamina, said film and lance device can be applied to the skin.

6. A test strip as in claim 5 wherein said lance device has a recessed surface forming a cavity, said at least one lance projecting from said recessed surface to a point outside said cavity.

7. A test strip as in claim 5 wherein said lance device is a generally semi-spherical structure having an imperforate dome-shaped body forming a concave cavity from which said at least one lance projects, said structure further having a peripheral flange around the cavity.

8. A test strip as in claim 5 including a plurality of spaced-apart lance devices, said flexible film, support lamina and closure lamina being common to all said lance devices.

9. A laminated test strip for allergy testing by a technique involving penetration of the allergen into the skin comprising: at least one lance device having at least one lance projecting therefrom; a flexible film having one surface carrying a pressure sensitive adhesive, said lance device being attached to said film such that said lance projects away from said surface which carries the pressure sensitive adhesive; a support lamina having an aperture extending therethrough in the thickness direction, said support lamina including a relatively thick layer of material and a thinner layer having a surface exhibiting non-stick properties, said thinner layer being bonded to one surface of said relatively thick layer with said non-stick surface facing outwardly, said flexible film being releasably sealed to said non-stick surface by said pressure-sensitive material and said lance device being so positioned that said lance projects into said aperture in said support lamina; and a closure lamina detachably secured to the surface of said support lamina opposite said flexible film so as to overlie said aperture in said support lamina, whereby upon removal of said closure lamina from said support lamina, allergen can be applied to said lance, and whereby removal of said film and its attached lance device from said support lamina, said film and lance device can be applied to the skin.

10. A test strip as in claim 9 wherein said lance device has a recessed surface forming a cavity, said at least one lance projecting from said recessed surface to a point outside said cavity.

11. A test strip as in claim 9 wherein said lance device is a generally semi-spherical structure having an imperforate dome-shaped body forming a concave cavity from which said at least one lance projects, said structure further having a peripheral flange around the cavity.

12. A test strip as in claim 9 including a plurality of spaced-apart lance devices, said flexible film, support lamina and closure lamina being common to all said lance devices.

13. A test strip for allergy testing by a technique involving penetration of an allergen into the skin comprising: at least one lance device having a body and at least one lance projecting from the body; a lance-carrying layer attached to the body of said lance device in a manner such that the lance projects away from said lance-carrying layer; an intermediate layer having opposite surfaces and an aperture extending therethrough from one surface to the other, said lance-carrying layer being releasably attached to one surface of said intermediate layer such that said lance projects into said aperture; and a closure layer releasably sealed to the opposite surface of said intermediate layer in overlying relationship with said aperture so as to prevent entry of foreign matter into said aperture.

14. A test strip as in claim 13 including a plurality of said lance devices carried in spaced-apart relationship by said lance-carrying layer, said lance-carrying layer being flexible and releasably attached to said one surface of said intermediate layer by pressure sensitive adhesive carried by said lance-carrying layer, and said intermediate layer having a plurality of said apertures corresponding to said lance devices.

* * * * *